United States Patent [19]

Reshef et al.

[11] Patent Number: 5,050,604
[45] Date of Patent: Sep. 24, 1991

[54] APPARATUS AND METHOD FOR MONITORING THE HEALTH CONDITION OF A SUBJECT

[76] Inventors: Israel Reshef, Hameri Street 38, 53330 Givatayim; Mordechai Erez, Sharsheret 19, 69697 Tel Aviv, both of Israel

[21] Appl. No.: 421,890

[22] Filed: Oct. 16, 1989

[51] Int. Cl.⁵ .............................................. A61B 5/00
[52] U.S. Cl. .................................... 128/632; 128/635; 128/760
[58] Field of Search ................ 128/632, 635, 760, 771

[56] References Cited

U.S. PATENT DOCUMENTS

| | | | |
|---|---|---|---|
| 3,635,213 | 1/1972 | LaHay | 128/632 |
| 4,195,641 | 4/1980 | Joines et al. | 128/632 |
| 4,822,336 | 4/1989 | DiTraglia | 128/635 X |

FOREIGN PATENT DOCUMENTS

| | | | |
|---|---|---|---|
| 2453631 | 12/1980 | France | 128/632 |
| 0135646 | 6/1986 | Japan | 128/760 |
| 0072321 | 4/1987 | Japan | 128/635 |
| 0031638 | 2/1988 | Japan | 128/635 |

OTHER PUBLICATIONS

Gibson et al., "Studies of Salt Excretion in Sweat", J. Pediatrics, Jun. 1963, pp. 855-867.

*Primary Examiner*—Lee S. Cohen
*Attorney, Agent, or Firm*—Benjamin J. Barish

[57] ABSTRACT

Apparatus for monitoring the health condition of a subject includes a sweat collector unit, a sweat analyzing device for analyzing the sweat collected by the sweat collector unit; and a body attaching device for attaching both the sweat collector unit and the sweat analyzing device to the body of a subject for collecting and analyzing the subject's sweat, thereby enabling the health of the subject to be continuously and non-invasively monitored.

14 Claims, 4 Drawing Sheets

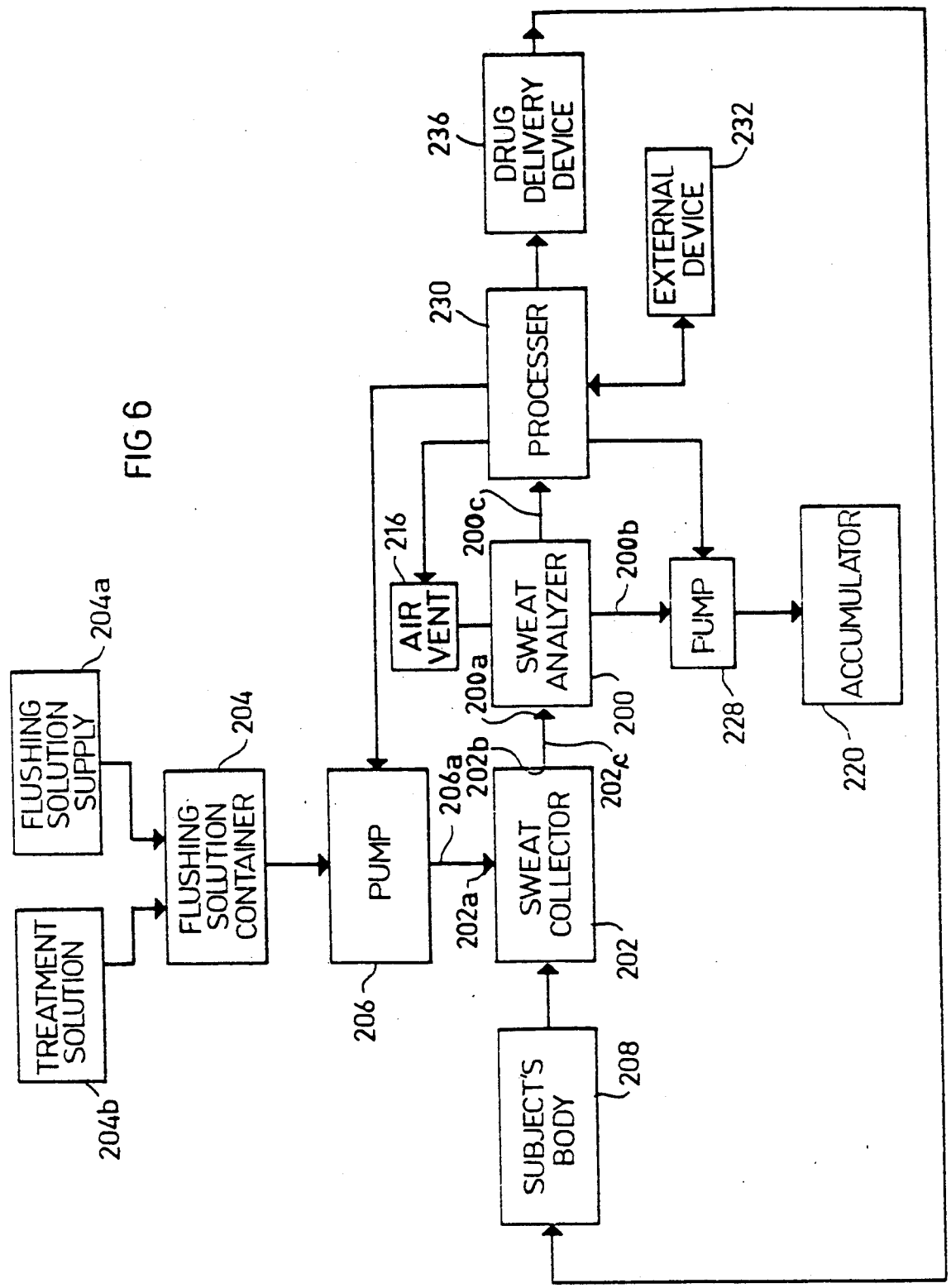

APPARATUS AND METHOD FOR MONITORING THE HEALTH CONDITION OF A SUBJECT

FIELD AND BACKGROUND OF THE INVENTION

The present invention relates to apparatus, and also to a method, for monitoring the health condition of a subject.

At the present time, there are three general techniques for monitoring the health condition of subjects: (1) physical techniques e.g., measurements of blood-pressure, pulse, body temperature, examination by x-rays, etc.; (2) chemical techniques, e g., chemical analysis of blood, urine, feces, etc.; and (3) biochemical and biological techniques, e.g., cytological, immunological, hematological and enzymological tests, etc. The above techniques are usually used in a complimentary manner according to the particular case.

While the physical techniques are generally non-invasive, and can be applied in a continuous manner if desired, this is not true of the chemical, biological, and biochemical techniques. For example, analyzing a blood sample requires not only invading the subject's body, but also basing the diagnosis on a momentary condition of the subject's body, namely when the sample was taken. While urine and feces analysis techniques are non-invasive, they reflect an average condition over the period of time during which the analyzed sample accumulated. Moreover, in all the foregoing chemical techniques, the diagnosis is generally not made on a real-time basis, since the sample is usually sent to a laboratory for analysis and therefore a delay is involved between the time at which the sample was taken and the time when a diagnosis can be made. Also, analysis in the laboratory runs the risk of mistakes in the correct identification of the sample analysed.

OBJECTS AND SUMMARY OF THE INVENTION

An object of the present invention is to provide an apparatus and also a method for monitoring the health condition of a subject, having a number of important advantages over the presently used diagnostic techniques.

According to the present invention, there is provided apparatus for monitoring the health condition of a subject, comprising: a sweat collector unit having an inlet and an outlet, a sweat analyzer unit having a liquid inlet and an electrical-signal outlet for outletting electrical signals corresponding to the analysis of the sweat therein, and a container for containing a flushing solution. First conduit means connects the container to the inlet of the sweat collector unit, and second conduit means connects the outlet of the sweat collector unit to the liquid inlet of the sweat analyzer unit, for introducing a flushing solution from the container into the sweat collector unit and for flushing the sweat collected therein to the sweat analyser unit. The apparatus further includes body attaching means for attaching the sweat collector unit and the sweat analyzer unit to the body of the subject for continuously collecting and analyzing the subject's sweat, and a processor for processing the electrical signals outletted by the sweat analyzer unit, for controlling the first conduit means in response thereto, and for providing a continuous indication of the health condition of the subject.

Apparatus constructed in accordance with the foregoing features thus permits monitoring the health condition of a subject in a non-invasive and real-time manner, providing an immediate and continuous indication of the subject's health condition. This continuous and immediate indication may be used for informational purposes to better inform the physician, or the subject himself, as to the subject's health condition, or it may be used for control purposes, e.g. for controlling, either non-automatically or automatically, the administering of a drug to the subject in response to the indicated health condition.

While sweat testing is known for diagnosing cystic fibrosis, the technique usually used is to stimulate sweating, e.g. by heat and/or by a sweat stimulation drug, to collect the sweat, and then to send the collected sweat to a laboratory for analysis, e.g., by using sodium and chloride ion-selective electrodes. Such known cystic-fibrosis technique however produces results which reflect the momentary condition of the subject and after the elapse of a time delay, i.e., from the time the sample was taken to the time it is analyzed, and therefore does not provide the advantages of continuity and immediacy of the present invention.

The analysis by the sweat analyzer unit may be effected by known techniques, such as ion-selective electrodes or other electrochemical, chemical, physical, or biolochemical techniques. In addition to analysing the collected sweat, the apparatus may also include a pH sensor for sensing the pH of the collected sweat, a temperature sensor for sensing the temperature of the sweat and/or of the skin at the sweat site or at another location, an electrical-conductivity sensor for sensing the electrical conductivity of the skin at the sweat site, etc., to provide additional information to be taken into consideration with the analysis of the collected sweat in order to indicate the health condition of the subject.

According to a further embodiment of the invention described below, the apparatus may further include drug administering means for administering a drug to the subject, and control means for controlling the drug administering means in response to the output of the sweat analyzer means. Such an apparatus could be used, for example, in administering insulin or other drug automatically in response to the instantaneous condition of the body.

The invention also provides a method for monitoring the health condition of the subject.

Further features and advantages of the invention will be apparent from the description below.

BRIEF DESCRIPTION OF THE DRAWINGS

The invention is herein described, by way of example only, with reference to the accompanying drawings, wherein:

FIG. 6 is a flow diagram illustrating the main components of a still further form of apparatus constructed in accordance with the invention.

DESCRIPTION OF PREFERRED EMBODIMENTS

Figure 1:
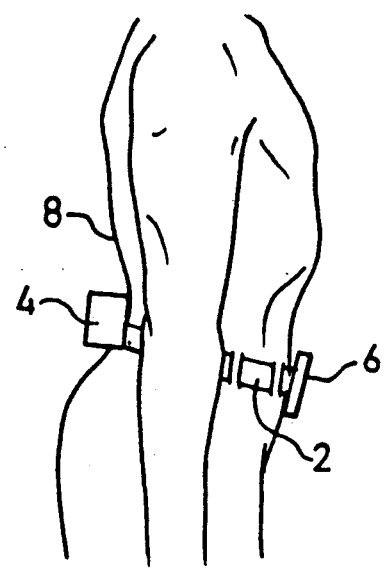
FIG. 1 illustrates one form of body-applied apparatus constructed in accordance with the invention for monitoring the health condition of a subject.

FIG. 1 schematically illustrates one form of apparatus constructed in accordance with the invention applied to the body 8 of the subject whose health condition is being monitored. The apparatus includes a belt 2 applied to the waist of the subject, a sweat collector unit 4 mounted to the belt and applied to the sweat site at the small of the subject's back, and a further unit 6 also mounted bY the belt 2. The sweat collector unit 4 also includes the sweat analyzer means; e.g., ion-selective electrodes as will be described more particularly below, whereas the further unit 6 includes the electronic circuitry for processing the information produced as a result of analyzing the collected sweat. The latter circuitry could include, for example, an analogue interface, an analogue-to-digital converter, a microprocessor, and a power supply, for analyzing the sweat absorbed by the sweat collector unit 4, and for producing an output indicating the health condition of the subject. Since all the foregoing equipment is continuously worn by the subject, the illustrated apparatus is not only non-invasive, but also produces an immediate and continuous indication of the subject's health condition.

Figure 2:
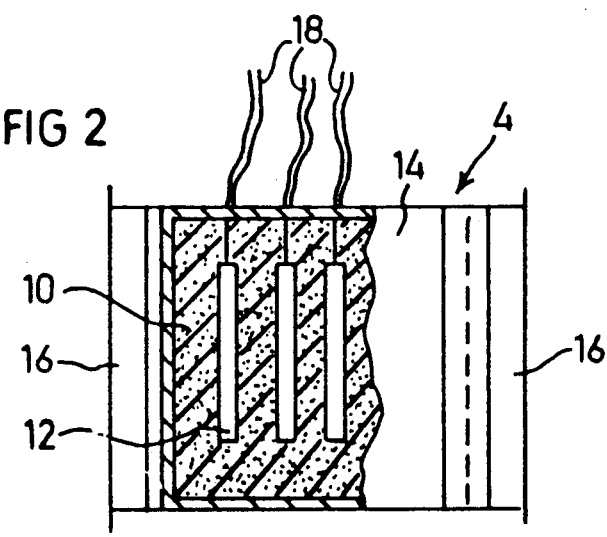
FIGS. 2 and 2a are top and side views, respectively, illustrating one form of combined sweat collecting and analyzing unit constructed in accordance with the invention for use in the apparatus of FIG. 1.
Figure 2A:
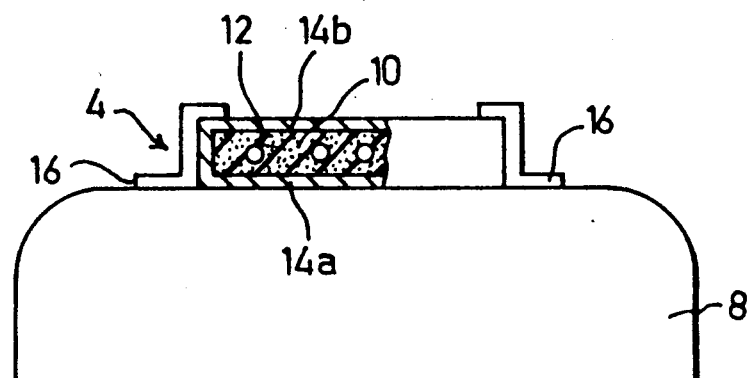

FIGS. 2 and 2a illustrate one form of a combined sweat collector and analyzer unit 4 which may be used in the apparatus of FIG. 1. In this embodiment, unit 4 is in the form of a pad which includes an absorbent material 10, such as cotton gauze or a sponge, containing a plurality of spaced electrodes 12 all enclosed within a sheath 14. Sheath 14 includes liquid-permeable inner layer 14a and an outer vapour permeable layer 14b, and is firmly secured against the skin of the subject by adhesive strips 16. The electrodes 12 are connected to a data processor unit 6 (FIG. 1) at the opposite side of the belt by means of electrical conductors 18.

It will be seen that the subject's sweat continuously passes through the liquid-permeable inner layer 14a of sheath 14 and is absorbed by the absorbent material 10 within unit 4. The vapour-only permeable outer layer 14b permits the absorbed sweat also to evaporate to the atmosphere. The condition of the sweat absorbed by absorbent 10 is continuously monitored by the electrodes 12 within unit 4, and this information is continuously fed via output conductors 18 to the data processor unit 6 worn by the subject. Unit 6 may include a microprocessor outputting the processed information to a display or to a storage device for displaying and/or storing the results of the analysis made by the processor connected to the electrodes 12 in unit 4.

The electrodes 12 within unit 4 include one or more ion-selective electrodes for detecting particular ions, such as sodium, potassium, calcium, magnesium, chloride, sulphate, carbonate, lactate or phosphate ions helpful in diagnosing particular conditions of the body. Such ion-selective electrodes are well known, and therefore further details of their construction and operation are not set forth herein.

Unit 4 may also include a pH sensitive electrode or probe for sensing the pH of the sweat absorbed by the unit. It may also include a temperature sensor and/or an electrical-conductivity sensor, for sensing the temperature and/or electrical conductivity of the skin at the sweat site In the embodiment illustrated in FIGS. 2 and 2a, there will be a tendency for the non-volatile constituents of the sweat absorbed by unit 4, such as sodium chloride, urea, lactic acid, and potassium salts, to accumulate within the unit. However, since the rate of accumulation of such constituents is continuously measured, this can be taken into account by the data processing unit 6 for indicating the health condition of the subject at any particular time.

Figure 3:
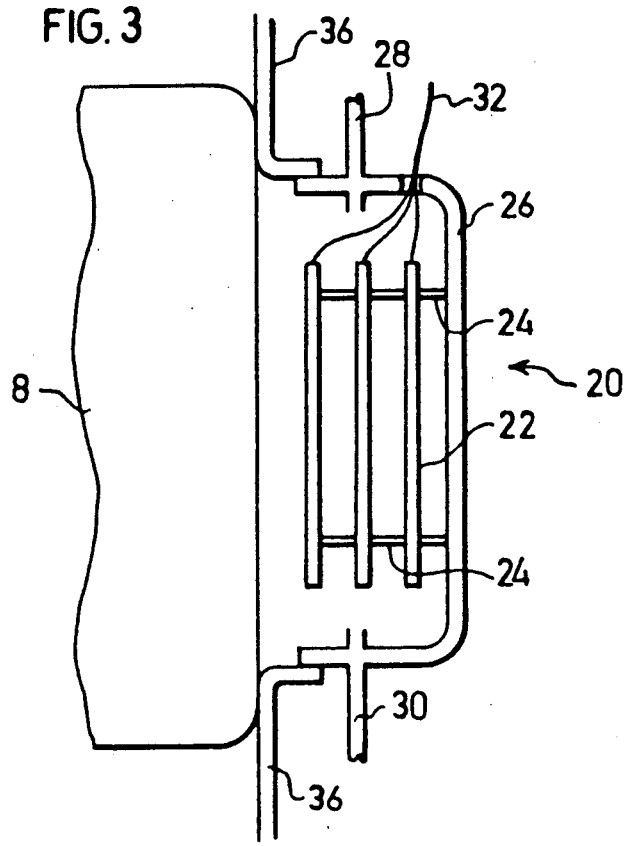
FIG. 3 is a side-elevational view illustrating another form of combined sweat collecting and analyzing unit which may be used in the apparatus of FIG. 1.

FIG. 3 illustrates another type of sweat collector unit 20, which may be used in place of unit 4 in the body-applied apparatus of FIG. 1. Unit 20 of FIG. 3 also includes the sweat analyzer means comprising a plurality of electrodes 22 mounted by a support 24 within a sheath 26 open at the side attached to the skin and sealed to the subject's body 8 by sealing strip 36. In this case, however, sheath 26 is liquid and vapour impermeable to prevent the passage of liquid and vapour therethrough to the atmosphere.

Unit 20 also includes an inlet 28 and an outlet 30 for a flushing solution. The flushing solution may be water having the same concentration of constituents as sweat, to serve as a reference value. Thus, the output appearing on the output conductors 32 of the electrodes 22 represents deviations from the reference value of the sweat received from the subject's body 8.

As in the above described FIG. 2 embodiment the electrodes 22 in the sweat collector unit 20 of FIG. 3 may include ion-selective electrodes for detecting one or more particular ions in the sweat, a pH sensitive electrode for detecting the pH of the sweat, a temperature-sensitive electrode for detecting the temperature of the sweat and/or of the skin at the sweat site, and/or an electrical-conductivity electrode for detecting the electrical conductivity of the skin at the sweat site.

Figure 4:
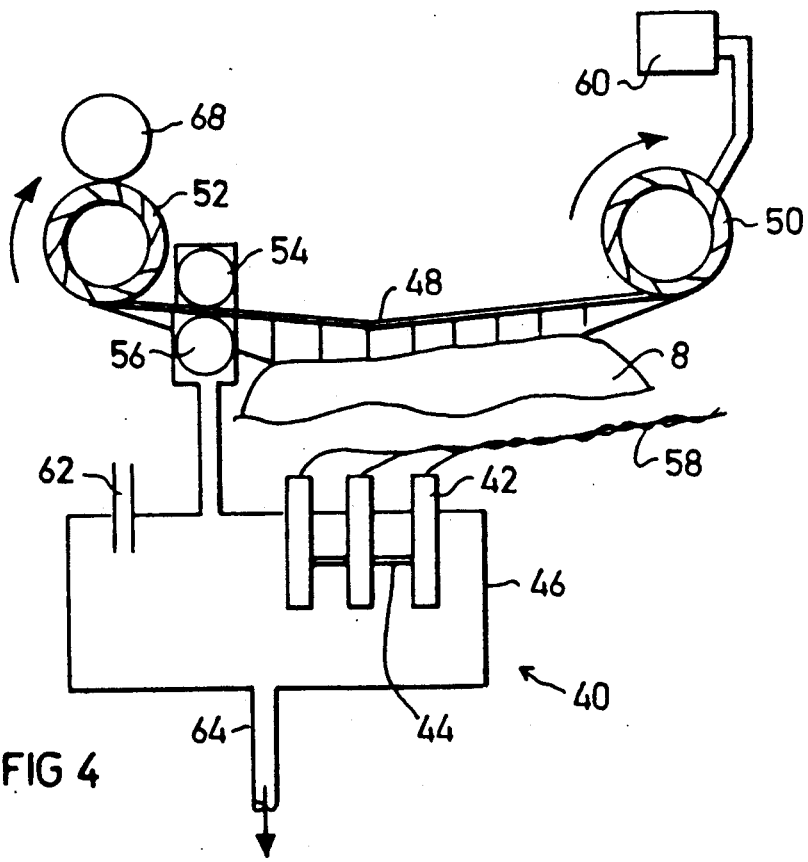
FIG. 4 schematically illustrates a still further form of apparatus constructed in accordance with the invention FIG. 5 schematically illustrates a still further form of apparatus constructed in accordance with the invention.

FIG. 4 illustrates a further arrangement which may be used in the body-mounted apparatus of FIG. 1. This arrangement also includes a sweat-analyzer unit 40 including a plurality of electrodes 42 mounted by support 44 housed within a sheath 46. In this case, the sweat is not collected directly from the subject's body 8, but rather from an absorbent strip 48 wound between a supply roll 50 and a take-up roll 52 driven by a motor 68. A stretch of the absorbent strip 48 is in contact with the skin of the subject's body 8 at the sweat site as the strip is driven from the supply roll 50 to the take-up roll 52, so as to absorb the sweat at that site. Before reaching the take-up roll 52, strip 48 is squeezed into the unit 40 for analysis by a pair of pressure rollers 54, 56.

Absorbent strip 48 is preferably pre-wetted by a liquid from source 60 before being brought into contact with the subject's skin. In addition, unit 40 includes a flushing inlet 62 and a flushing outlet 64 for flushing the unit, as described above with respect to FIG. 3. The solution used for wetting absorbent strip 48 and for flushing unit 40 may also be of the composition of sweat to serve as reference, as described above with respect to FIG. 3, so that the output of unit 40 will represent deviations of the absorbed sweat from the reference value. Electrodes 42 in unit 40 may also be of the type described in the embodiments of FIGS. 2 and 3.

It will thus be seen that unit 40 in FIG. 4 also constitutes a sweat collector unit, but in this case the sweat is not collected directly from the subject's body, but rather indirectly via the absorbent strip 48. It will also be seen that the sweat collector unit 40 includes sweat analyzer means, namely the electrodes 42, which analyze the composition of the sweat collected in unit 40. The results of the analysis made by electrodes 42 may be outputted through wires 58 to a data processor unit (not shown), which would correspond to unit 6 in FIG. 1, also worn by the subject.

Figure 5:
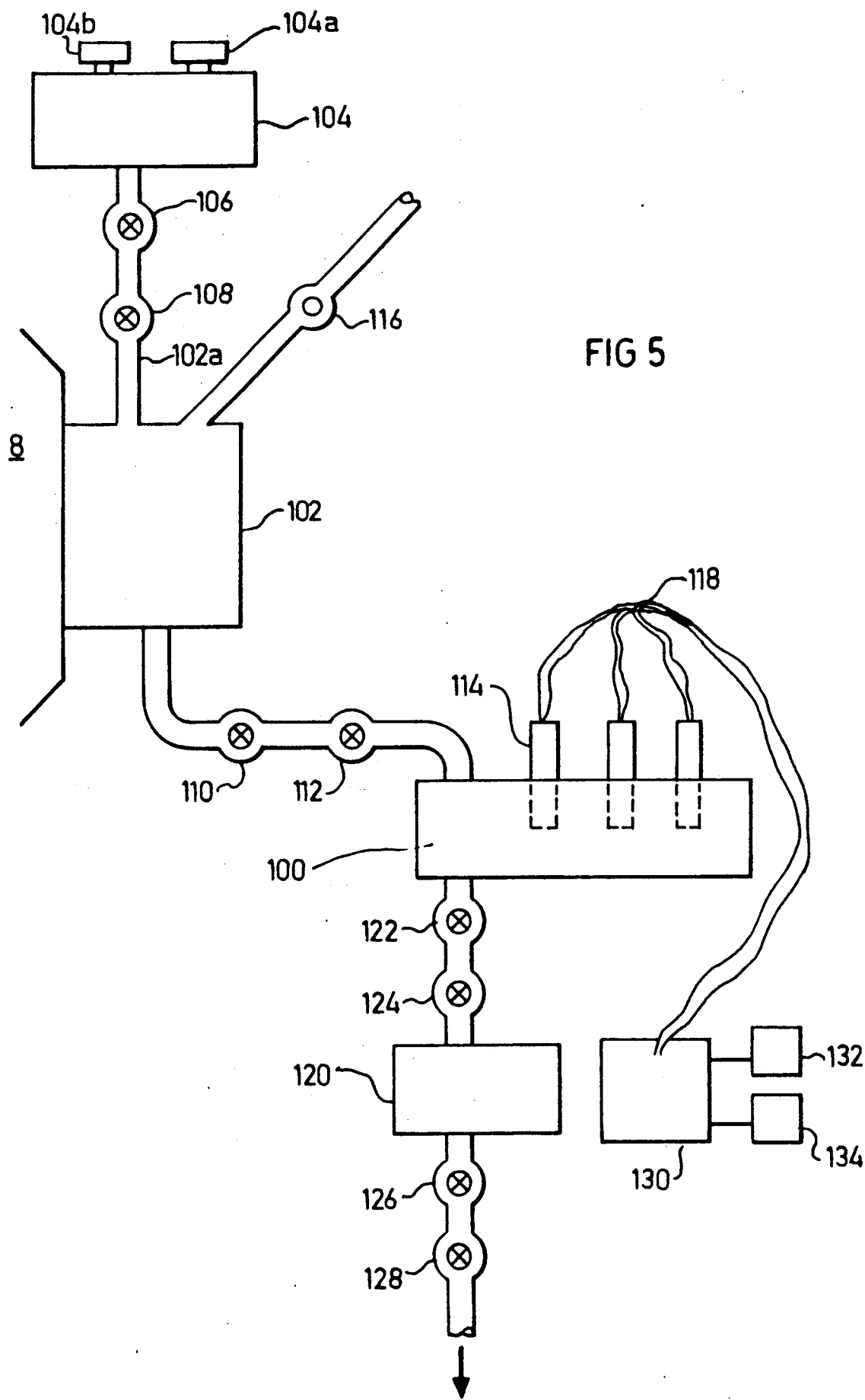

FIG. 5 illustrates another form of apparatus wherein the sweat analyzer means, therein designated 100, is included in a unit which is separate and distinct from the sweat collector unit, therein designated 102. Both units are worn by the subject so as to enable the composition of the subject's sweat to be continuously analyzed, and thereby to provide an immediate and continuous indication of the subject's health condition.

The sweat collector unit 102 illustrated in FIG. 5 is also in the form of a sheath or container open at one side and pressed against the subject's skin so as to permit the sweat thereat to be collected for analysis. The apparatus further includes a detachable source of a flushing solution 104 connected to an inlet 102a of the sweat collector unit 102 via pump 106 and a valve 108 enabling control of the flow of the flushing solution into the sweat collector unit 102. The source of flushing solution 104 includes an inlet 104a, such as a removable filler cap for introducing the flushing solution into the unit, and a second inlet 104b, such as a needle-pierceable septum, for injecting a treatment material, such as a sensitivity testing material, into the flushing solution.

The flushing solution pumped into the collector unit 102 is pumped out of that unit via another pump 110 and a valve 112 into the sweat analyzer unit 100. The latter unit containing a plurality of electrodes 114 for analyzing the composition of the flushing solution and sweat introduced into that unit. Unit 100 may also include an absorbent material for absorbing the solution during its analysis by the electrodes 114, but preferably does not include such an absorbent material so that the electrodes are immersed in a solution pumped into that unit. To facilitate pumping the solution out of the sweat collector unit 102 into the sweat analyzer unit 100, the sweat collector unit 102 may include an air vent 116. In addition, the electrodes 114 of the sweat analyzer unit 100 would be connected to a data processor unit (not shown), also worn by the subject, if the subject is mobile, to provide a continuous indication of the composition of the sweat collected by unit 102, and thereby an immediate and continuous indication of the subject's health condition. Alternatively, if the subject is not mobile, e.g., on a hospital bed, the data processor unit connected to electrodes 114 may be in a separate unit not worn by the subject but connected to the sweat analyzer electrodes 114 by electrical conductors 118.

The apparatus illustrated in FIG. 5 further includes a container 120 connected to the sweat analyzer unit 100 by a further pump 122 and valve 124 for accumulating the solution flushed through the sweat collector unit 102 and sweat analyzer unit 100. Container 120 is preferably detachable from unit 100 to permit the solution accumulated therein to be detached from the subject so that the solution accumulated therein may be periodically dumped or further analyzed, e.g., in a laboratory, if desired. Alternatively, the solution in accumulator container 120 may be periodically transferred by another pump 126, and by another valve 128, for external analysis, e.g., in a laboratory.

The apparatus illustrated in FIG. 5 may also include a processor 130 having inputs connected to the electrode 114 of the sweat analyzer unit 100, and outputs to the pumps 106, 110, 122 and 126, and their corresponding valves 108, 112, 124 and 128, and air vent 116, so as to precisely control the transfer of the solutions through the various units, as well as to effect self-cleaning and/or automatic calibration of these units. Processor 130 also processes the data regarding the composition of the collected sweat as outputted from electrodes 114 of the sweat analyzer unit 100, and produces an output, e.g., to a display 132 and/or an external communication channel 134. As indicated earlier, processor 130 may also be worn by the subject when the subject is mobile, or incorporated in a separate unit not worn by the subject when the subject is not mobile, e.g., on a hospital bed. It will also be appreciated that in the latter case, processor 130 may serve a plurality of subjects in a hospital ward so as to permit monitoring a plurality of subjects at a central location.

As indicated earlier, the above-described apparatus may be used for providing a continuous and instantaneous indication of the health condition of the subject for diagnostic purposes. Such apparatus may also be used for treating the subject, e.g. for automatically controlling a drug administering device, such as a micropump, in response to the sensed condition of the subject or subjects. FIG. 6 is a block diagram illustrating a system for the above purpose.

Thus, the system illustrated in FIG. 6 also includes a sweat analyzer unit 200 separate and distinct from the sweat collector unit 202, both corresponding to units 100 and 102, respectively, in FIG. 5, for collecting and analyzing the sweat of the subject. The sweat collector unit includes an inlet 202a and an outlet 202b connected by a conduit 202c to an inlet 200a of the sweat analyzer unit 200. The sweat analyzer unit 200 in turn includes a liquid outlet 200b, and an electrical-signal outlet 200c for outletting the electrical signals, corresponding to the analysis of the sweat therein, to processor 230.

The inlet 202a is supplied with flushing solution via a pump 206 and a conduit 206a. The flushing solution for flushing the sweat collector unit 202 is supplied from a detachable container 204 having a first inlet 204a for filling the container with the flushing solution, and a second inlet 204b, such as a needle-pierceable septum for adding a treatment material to the flushing solution, the flushing solution being pumped by pump 206 (e.g., a peristaltic pump) from container 204 into the sweat collector unit 202.

The sweat collected by unit 202 from the subject's body, schematically indicated at 208, is continuously analyzed by the sweat analyzer unit 200 (containing the electrodes 114, FIG. 5), and the analysis results processed by processor 230 and outputted to an external communication device 232, e.g., display 132 and/or external communication channel 134, FIG. 5. Processor 230 also controls, via pump 206, and air vent 216, the transfer of the flushing solution from container 204 to the sweat collector unit 202, as described above with respect to FIG. 5.

Processor 230, however, further controls a drug delivery device 236, such as a micropump, for delivering a drug to the subject 208 automatically in response to the chemical composition of the sweat (line connecting 208 to 202 in FIG. 6) as detected by the sweat analyzer unit 200. For example, if the apparatus is used for monitoring the subject with respect to cardiovascular diseases, the calcium concentration of the sweat collected by unit 202 may be continuously monitored and used for automatically controlling the delivery of an appropriate drug in response to the detected condition of the patient. Another example would be to detect the sugars concentration of the subject's sweat and controlling the delivery of insulin automatically in response to the detected condition. It will be appreciated that other conditions could be monitored and the appropriate drug delivered to the subject automatically in response to the detected condition.

As described above with respect to FIG. 5, the collected sweat and flushing solution may be periodically transferred by pump 228 (e.g., a peristaltic pump) from the sweat analyzer unit 200 to a detachable accumulator container 220, also under the control of processor 230.

While the invention has been described with respect to several preferred embodiments, it will be appreciated that these are set forth purely for purposes of example, and that many other variations, may be made. For example, instead of using ionselective electrodes for the analysis, there may be used optical spectroscopy, atomic absorption, immunological or other analysis techniques. The sweat analysis maY also be performed together with other diagnostic methods and instruments, such as portable ECG instruments. Many other variations, modifications and applications of the invention may be made.

What is claimed is:

1. Apparatus for monitoring the health condition of a subject, comprising:
    a sweat collector unit having an inlet and an outlet;
    a sweat analyzer unit having a liquid inlet and an electrical-signal outlet for outletting electrical signals corresponding to the analysis of the sweat therein;
    a container for containing a flushing solution;
    first conduit means connecting said container to the inlet of said sweat collector unit, and second conduit means for connecting the outlet of said sweat collector unit to the liquid inlet of said sweat analyzer unit, for introducing a flushing solution from said container into the sweat collector unit, and for flushing the sweat collected therein to said sweat analyzer unit;
    body attaching means for attaching said sweat collector unit and said sweat analyzer unit to the body of the subject for continuously collecting and analyzing the subject's sweat;
    and processor means for processing the electrical signals outletted by the sweat analyser unit, for controlling said first conduit means in response thereto, and for providing a continuous indication of the health condition of the subject.

2. The apparatus according to claim 1, wherein said sweat analyzer unit includes an ion-selective electrode for detecting a particular ion in the collected sweat.

3. The apparatus according to claim 1, wherein said body attaching means comprises a belt or jacket worn by the subject with the sweat collector unit in contact with the small of the subject's back.

4. The apparatus according to claim 1, wherein said first conduit means includes a pump, and said processor controls said pump in response to the electrical signals outletted by said sweat analyzer unit.

5. The apparatus according to claim 1, wherein said body attaching means also attaches said processor and said first and second conduit means to the subject.

6. The apparatus according to claim 1, wherein said sweat collector unit also includes an air vent, and said processor also controls said air vent in response to the electrical signals outletted by said sweat analyzer unit.

7. The apparatus according to claim 1, wherein said apparatus further includes drug delivery means for delivering a drug to the subject, and said processor also controls said drug delivery means in response to the electrical signal outletted by said sweat analyzer unit.

8. The apparatus according to claim 1, wherein said sweat analyzer unit includes a liquid outlet, and said apparatus further includes an accumulator and further conduit means connecting said latter liquid outlet to said accumulator, said processor also controlling said further conduit means in response to the electrical signals outletted by said sweat analyzer unit.

9. The apparatus according to claim 1, wherein said container includes a first inlet for the flushing solution, and a second inlet for a treatment solution.

10. A method of monitoring the health condition of a subject, comprising:
    attaching to the body of the subject the apparatus as defined in claim 1 with the collector unit engaging a sweat site thereof;
    introducing a flushing solution from the container into the sweat collector unit;
    flushing the sweat collected in the sweat collector unit to the sweat analyzer unit;
    and analyzing by the processor means the naturally-produced sweat of the subject collected in the analyzer unit to thereby continuously indicate the health condition of the subject.

11. The method according to claim 10, wherein the analyzing of the collected sweat includes detecting one or more particular ions therein.

12. The method according to claim 10, wherein the analyzing of the collected sweat includes detecting the pH thereof.

13. The method according to claim 10, further including measuring the temperature of the subject's body and/or of the sweat in the analyzer unit.

14. The method according to claim 10, further including measuring the electrical conductivity of the skin at the sweat site.

* * * * *